United States Patent [19]
Ng

[11] Patent Number: 5,674,341
[45] Date of Patent: Oct. 7, 1997

[54] APPLICATION OF ADHESIVE TO A NON-PLANAR SURFACE

[75] Inventor: Anthony C. Ng, East Brunswick, N.J.

[73] Assignee: McNeil-PPC, Inc., Skillman, N.J.

[21] Appl. No.: 449,510

[22] Filed: May 23, 1995

Related U.S. Application Data

[63] Continuation of Ser. No. 20,484, Feb. 22, 1993, abandoned.

[51] Int. Cl.$^6$ .............................. A61F 13/15; B44C 00/00
[52] U.S. Cl. ................... 156/234; 156/238; 156/240; 156/230; 604/366; 604/380; 604/381; 604/390
[58] Field of Search ..................... 156/230, 234, 156/240, 238, 540, 66; 602/54–58, 903; 604/365, 366, 379, 386, 387, 389, 390, 383

[56] References Cited

U.S. PATENT DOCUMENTS

| | | | |
|---|---|---|---|
| 3,060,936 | 10/1962 | Burgeni | 604/365 |
| 3,688,771 | 9/1972 | Werner | 604/387 |
| 3,788,271 | 1/1974 | Carpenter | 118/33 |
| 3,874,984 | 4/1975 | Newman | 161/117 |
| 3,888,255 | 6/1975 | Shah et al. | 128/290 |
| 4,023,570 | 5/1977 | Chinai et al. | 604/390 |
| 4,151,319 | 4/1979 | Sackoff et al. | 428/40 |
| 4,376,440 | 3/1983 | Whitehead et al. | 604/387 |
| 4,388,137 | 6/1983 | McCarty et al. | 156/275 |
| 4,463,704 | 8/1984 | Farnam | 118/642 |
| 4,466,993 | 8/1984 | Hsu et al. | 427/44 |
| 4,475,913 | 10/1984 | Hlaban | 604/387 |
| 4,496,618 | 1/1985 | Pernicano | 428/201 |
| 4,501,772 | 2/1985 | Luxeder | 427/208.6 |
| 4,517,237 | 5/1985 | Pernicano | 428/198 |
| 4,530,353 | 7/1985 | Lauritzen | 128/156 |
| 4,540,415 | 9/1985 | Korpman | 604/390 |
| 4,622,089 | 11/1986 | Lauritzen | 156/250 |
| 4,627,847 | 12/1986 | Puletti | 604/366 |
| 4,664,735 | 5/1987 | Pernicano | 156/240 |
| 4,675,211 | 6/1987 | Thoma et al. | 427/208.8 |
| 4,692,161 | 9/1987 | Puletti et al. | 604/366 |
| 4,718,898 | 1/1988 | Puletti et al. | 604/366 |
| 4,741,929 | 5/1988 | Kossuth | 427/258 |
| 4,765,858 | 8/1988 | Vankerckhoven et al. | 156/235 |
| 4,867,818 | 9/1989 | Morgan | 156/80 |
| 4,894,259 | 1/1990 | Kuller | 427/208.8 |
| 4,946,527 | 8/1990 | Battrell | 156/60 |
| 4,959,265 | 9/1990 | Wood et al. | 604/389 |
| 5,037,668 | 8/1991 | Nagy | 427/44 |
| 5,128,187 | 7/1992 | Polski | 428/40 |
| 5,133,998 | 7/1992 | Okazaki et al. | 427/428 |

*Primary Examiner*—John G. Weiss
*Assistant Examiner*—K. M. Reichle

[57] ABSTRACT

A disposable panty shield has a thin, highly absorbent pad having a body-contacting surface, an absorbent layer, a liquid barrier, an adhesive layer, and a release layer to protect the positioning adhesive prior to use wherein the panty shield has been densified by fusing all pad layers together in a manner such that the interstitial space between the individual fibers in the densified areas is not sufficient to readily allow fluid to flow through, and the liquid barrier has a contoured surface. The adhesive layer is attached to the liquid barrier such that the adhesive follows the contour of the liquid barrier.

7 Claims, 7 Drawing Sheets

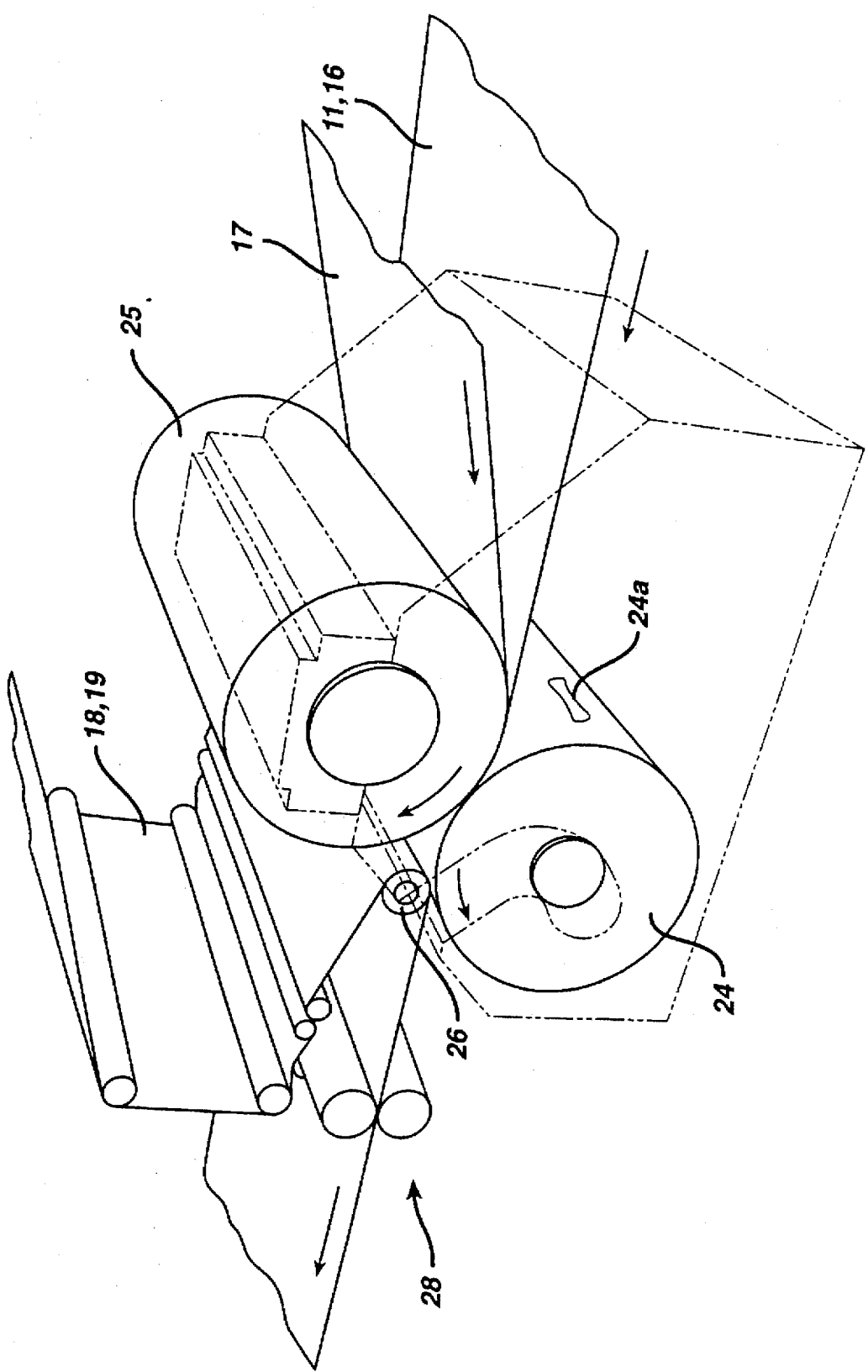

APPLICATION OF ADHESIVE TO A NON-PLANAR SURFACE

This is a continuation of application Ser. No. 08/020,484, filed Feb. 22, 1993 now abandoned.

BACKGROUND OF THE INVENTION

The present invention relates to an absorbent article particularly suited for everyday feminine hygiene and for protecting an undergarment against staining from light, daily secretions and discharges. It comprises a very thin, lightweight, highly absorbent pad which is soft, supple and easily conformable to the body and the garment to which it is adhesively attached. More particularly, the article comprises a garment side surface which contains recesses and an adhesive layer which contacts and follows the contours of this surface including the recesses. The present invention further relates to an apparatus and method for manufacturing an absorbent article, which article comprises a garment side surface containing recesses and an adhesive layer which contacts and follows the contours of the garment side surface including the recesses.

The prior art is replete with patents relating to protective pads and shields since the protection of undergarments from staining, especially for the many women who are troubled with frequent, light bodily discharges, has been a long standing problem. These patents generally describe layered structures having a porous body contacting layer overlying a liquid impermeable garment side barrier layer, and a layer of absorbent material between the body contacting layer and the barrier layer. An adhesive is attached to the garment side of the fluid barrier to secure the assembled shield to the crotch portion of an undergarment. And, a release layer is removably affixed to the adhesive layer to keep the adhesive from making contact to anything until it is placed in the undergarment.

As for the materials of construction of the absorbent pad, body-contacting layers of the prior art include absorbent, porous, dry-laid, nonwoven webs or scrim type materials such as those described by I. S. Ness in U.S. Pat. No. 4,880,419 and by Campau in U.S. Pat. No. 3,044,467, Hendricks in U.S. Pat. No. 3,463,154 and Sneider in U.S. Pat. No. 3,570,491. Such materials are often coarse textured and harsh to the touch and, because of their absorbency, wet from the top surface down during use resulting in a constantly moist surface against the skin.

Body-contacting layers of the prior art such as those described by T. J. Luceri in U.S. Pat. No. 4,795,455, by S. Cadieux in European Patent No. 354,502, by A. T. Mays in European Patent No. 70,163, and by R. P. James in U.S. Pat. No. 4,368,323 include nonwovens made from hydrophobic fibers which have been coated with an adhesive or have been subjected to heat and/or pressure to fuse the individual fibers to each other. Such materials tend to have only limited absorption but serve to allow passage to lower layers for absorption and retention. As a result, the fluid is wicked away from the body, leaving the surface of the body-contacting layer feeling dryer to the touch.

The use of hydrophobic fibers for the body contacting layer allows fluid to pass through to the absorbent layer beneath yet will not retain moisture on the surface layer, thus providing greater comfort to the wearer by feeling dry for a longer period of time. The desirability of such a feature has been recognized by Levesque U.S. Pat. No. 3,838,692 who describes a chemical method of providing porosity to hydrophobic materials.

The absorbent layers taught by the prior art usually consists of pulp fluff as described by S. L. Kopolow in U.S. Pat. Nos. 4,552,618 and 4,555,192, by D. C. Holtman in U.S. Pat. Nos. 4,544,596 and 4,536,432, by P. K. Chatterjee in U.S. Pat. No. 4,474,949.

Alternatively, the absorbent layer of the prior art may consist of blends of pulp fluff and synthetic fibers as described by Malaney in U.S. Pat. Nos. 4,756,786 and in 4,684,570. Or, the absorbent layer may be thermoplastic fibers co-formed with pulp fibers.

It is also possible to disperse into the absorbent layer a super absorbent polymer such as those taught by S. Dabi in U.S. Pat. No. 4,494,963, by I. S. Ness in U.S. Pat. No. 4,880,419 and by J. Roller in U.S. Pat. No. 4,443,492.

The liquid impermeable barrier layer, located between the absorbent layer and the garment, is commonly made of polyethylene, polypropylene, or a like material. Such layers are taught in U.S. Pat. No. 4,731,066 by R. Korpman.

Generally, the earlier prior art teaches absorbent pads made of wood pulp fluff that, when properly manufactured to absorb large quantities of fluid, are thick and bulky. Recent developments in the art teach the use of materials such as sphagnum peat moss (such as that taught by Y. Levesque in U.S. Pat. No. 4,507,122) and super absorbent polymers which, pound for pound, absorb much greater quantities of fluid than pulp allowing for the manufacture of much thinner absorbent pads.

The prior art also teaches the application of heat and/or pressure to bind the fibers of the absorbent layer together into densified areas. As fluid makes contact with such densified areas, the fluid tends to wick across the layer, away from the point of fluid introduction. This action helps to inhibit local saturation of the pad which is one cause of pad failure. See, for example, U.S. Pat. No. 4,059,114 to Richards and U.S. Pat. No. 4,886,697 to Perdelwitz et al., both of which are incorporated by reference.

Once fluid has been introduced to the body contacting surface, pad construction is designed to cause the fluid to flow into the absorbent layer and remain there until disposal of the pad. However, the garment side layer of the structure is usually a liquid impermeable barrier layer which, in the event fluid continues to flow through the pad to the garment side, prevents leakage onto the wearer's undergarments.

While such prior art pads undoubtedly function to protect the undergarments to which they are applied, they are deficient in one primary area of performance. They tend to draw fluid toward the lateral and longitudinal edges of the pad, increasing the likelihood of failure by allowing leakage off the pad onto the wearer's clothes.

More recently, absorbent pads have been developed which form fluid barriers, both on the periphery of the pad and internally, to prevent or at least hinder fluid from migrating to the edge of the pad and leaking onto the wearer's undergarments. Such pads are of multi-layer construction and, optimally, contain fusible fibers in each layer. The fluid barriers are formed by thermally fusing all layers of the pad together in the z-direction (herein defined as the direction through the pad from the body side to the garment side); heat and pressure are selectively applied to cause the fusible fibers to melt and flow into the interstitial spaces between the non-melted fibers. By eliminating the capillary space, fluid flow through the fused areas is eliminated or greatly reduced. See, for instance, U.S. Pat. No. 4,886,697 (Perdelwitz, et al.) and U.S. patent application Ser. No. 07/960,664, entitled "Garment Shield" and assigned to the same assignee as the present invention.

However, the product described above, especially in thin products, causes the outer layers of the pad (both the body side and garment side surfaces) to become compressed at the areas where heat and pressure are applied. This results in a pad where recesses develop. That is, when looking at the pad in cross-section, the outer surfaces of the pad will curve in the z-direction toward the center of the pad. This is not generally a problem on the body side surface of the pad. In fact, many prior art references exist which call for densification of this surface.

On the garment side surface, however, problems can develop if the surface is not planar. Common commercial practice calls for a positioning adhesive to be applied to the garment side surface to keep the pad in place during use. Such adhesives are, typically, applied by a transfer coating process where the adhesive is first applied to release paper. The adhesive side of the release paper is then brought into contact with the garment side surface of the pad. Because the release paper, typically coated with silicone, has a lower release energy the adhesive will preferentially stick to the garment side surface of the pad. Further, the adhesive is chosen to preferentially stick to the garment side surface of the pad during use, so that when the pad is removed from the wearer's undergarments adhesive will not be left on the wearer's clothes. Such products and processes are taught by Balinth in U.S. Pat. No. 4,335,026; Korpman in U.S. Pat. No. 4,554,191; U.S. Pat. No. 4,946,527, assigned to Proctor & Gamble; U.S. Pat. No. 4,615,696, assigned to Kimberly Clark; all herein incorporated by reference.

If, however, the garment side surface contains one or more recesses the adhesive, when transferred from the release paper to the pad, will bridge the gap across the recess and not come into contact with the surfaces which define the recess. As a result, the adhesive at the recess will either be removed when the release paper is removed from the pad or, more likely, will preferentially stick to the wearer's clothes when the pad is removed after use. The present invention solves this problem.

Additionally, in the step of fusing the layers of an absorbent pad together, it has been discovered that small holes (pinholes) will commonly develop in the garment side (barrier) layer. Thus, in forming a fluid barrier to keep fluid from flowing toward the edges of the pad, the chances of failure through the barrier in the z-direction are increased. Thus, in the event pinholes are created in the barrier layer, it is necessary to find a way to keep fluid from flowing through such holes. The present invention solves this problem.

SUMMARY OF THE INVENTION

The disposable shield of the present invention comprises a thin, highly absorbent pad having a body-contacting surface, an absorbent layer, a liquid barrier, an adhesive layer for attaching the pad to an undergarment, and a release paper to protect the adhesive layer prior to use. The pad further comprises densified areas, at or near the periphery and in the section of the pad nearer the middle, which have been made by fusing all pad layers together in a manner such that the interstitial space between the individual fibers in the densified areas is insufficient to readily allow fluid to flow through. The densified areas are made contiguous such that fluid, when introduced or deposited on the pad, will be prevented or hindered from flowing to the edges of the pad. Further, at the densified areas, the garment side surface contains recesses wherein the garment side surface curves toward the cross-sectional mid-plane of the pad.

The present invention also involves a method of manufacturing an absorbent pad by applying heat and pressure to fuse all three layers of the pad—the body contacting layer, the absorbent layer, and the garment side layer—together, and applying an adhesive layer to the garment side layer wherein the adhesive layer is in contact with the garment side layer at the areas where all layers are fused together.

The present invention also involves an apparatus for applying adhesive to recessed areas of an absorbent article comprising a pattern roll, a anvil roll, and a transfer roll; wherein the longitudinal shafts of each roll are parallel to the other rolls, the anvil roll and transfer roll are each rollingly engaged with the pattern roll, the anvil roll has a smooth surface, the pattern roll has protuberances extending radially outwardly from the pattern roll but which do not make contact with the anvil roll, and the transfer roll is of a material that is softer than the pattern roll.

BRIEF DESCRIPTION OF THE DRAWINGS

In the accompanying diagrammatic drawings which illustrate the invention:

FIG. 8 is an isometric view of the process of the present invention.

DETAILED DESCRIPTION OF THE INVENTION

Figure 1:
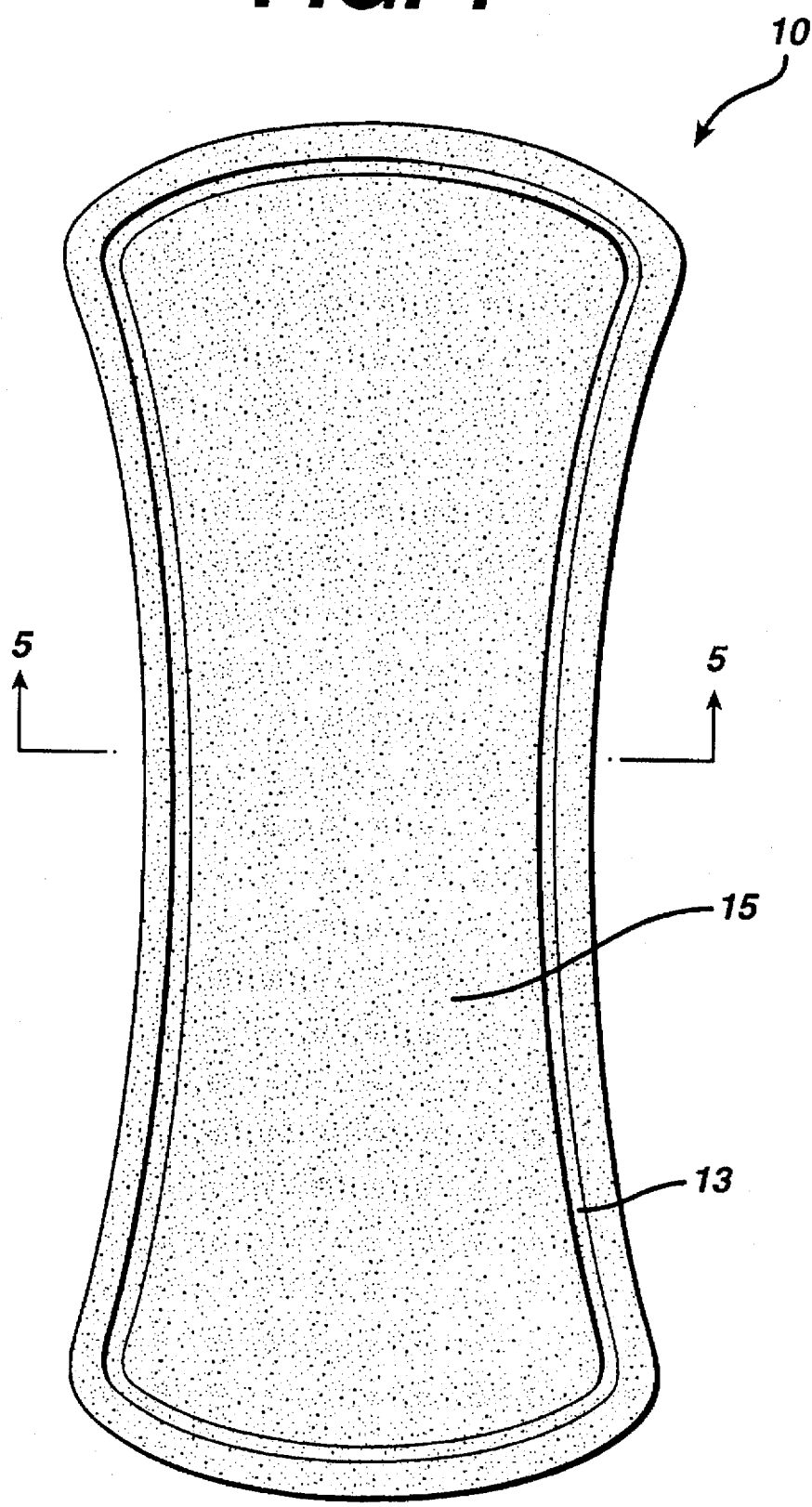
FIG. 1 is a plan view of one embodiment of a pad of the present invention.

Referring now more particularly to the drawings, FIG. 1 shows a pad 10 of the present invention in plan view. The pad there shown has an outer fluid barrier 13 near the perimeter of the pad which serves to prevent or greatly hinder fluid, which has been deposited on the pad, from flowing to the edge of the pad. Thus, the fluid is contained within the absorbing area 15.

Figure 2:
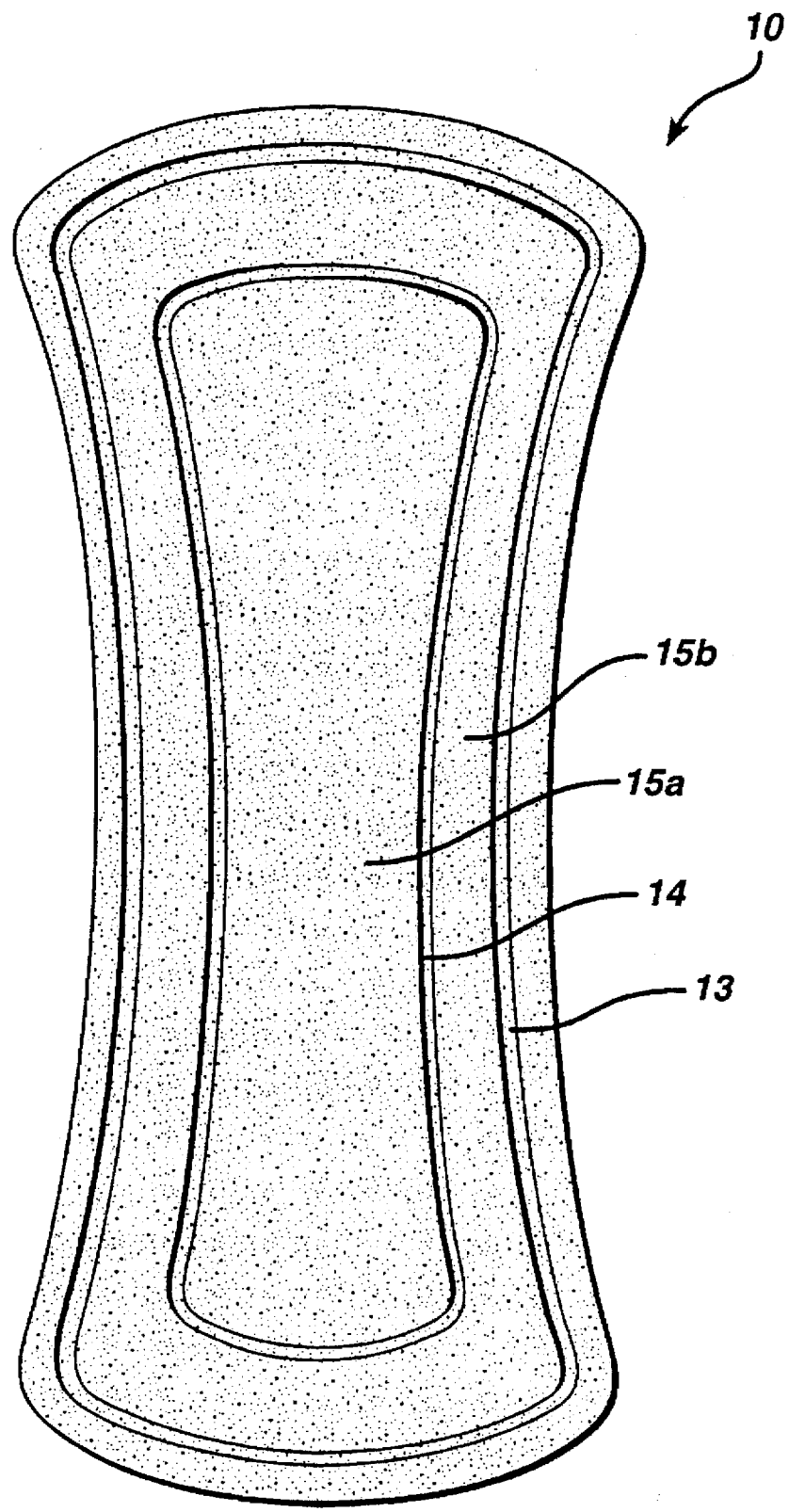
FIGS. 2 through 4 are plan views of further embodiments of the present invention.
Figure 3:
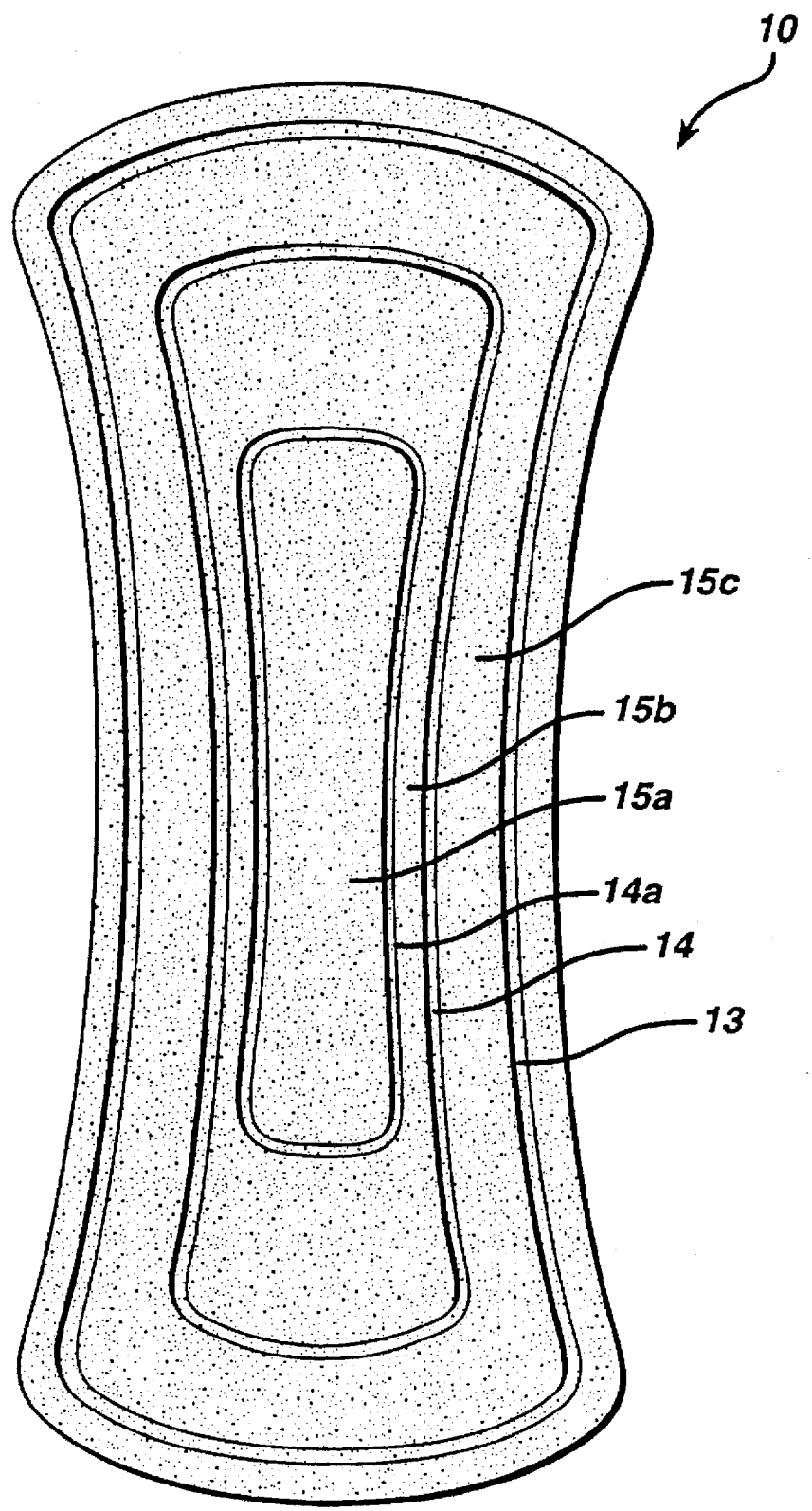
Figure 4:
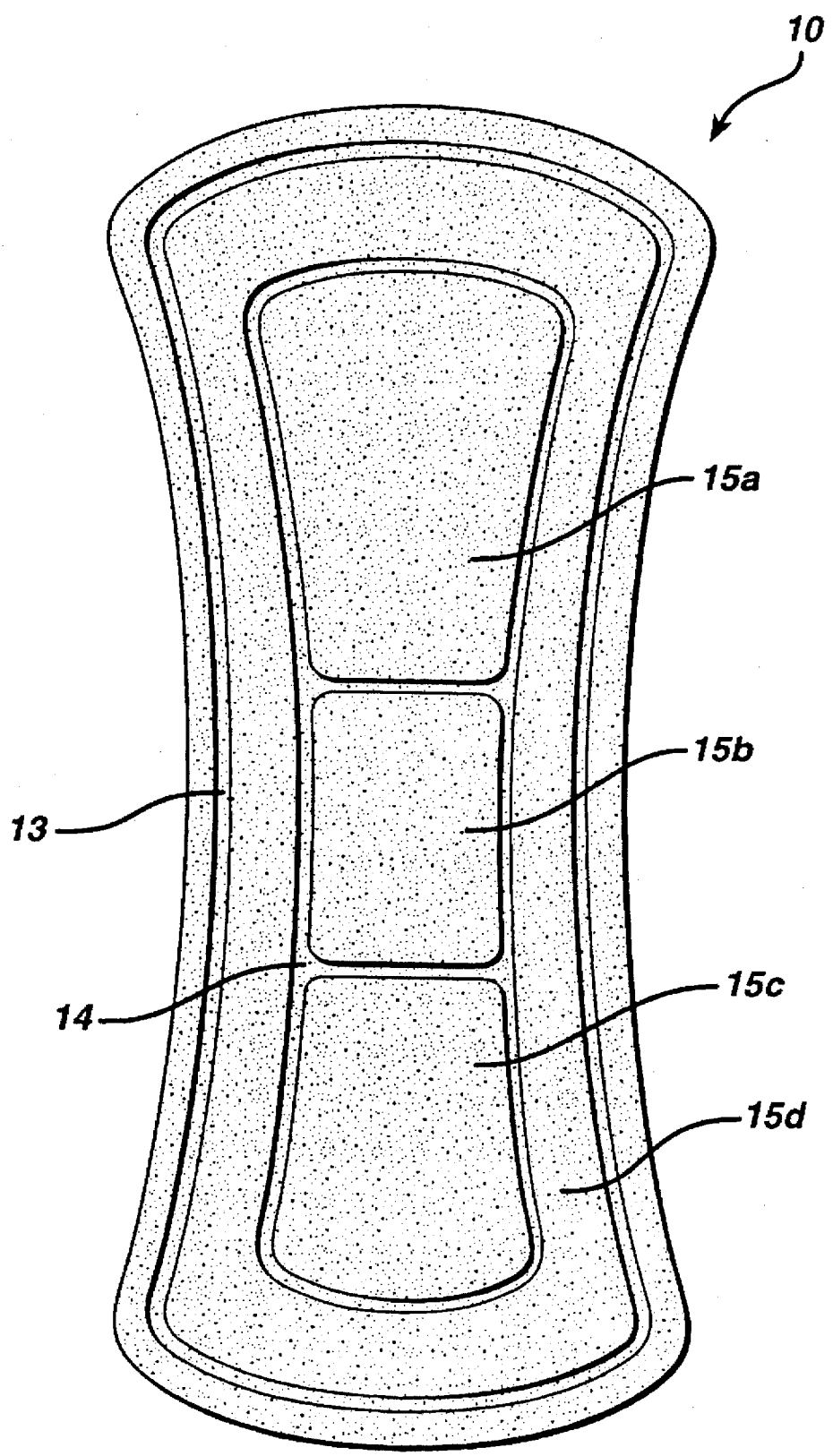

Referring to FIGS. 2 through 4, additional fluid barriers 14 and 14a are shown internal to fluid barrier 13. The purpose of these barriers is to separate, or compartmentalize, the pad into distinct absorbing areas 15a, 15b, 15c and 15d and to decrease the likelihood that fluid will migrate past fluid barrier 13. Many others designs will suggest themselves.

Figure 5:
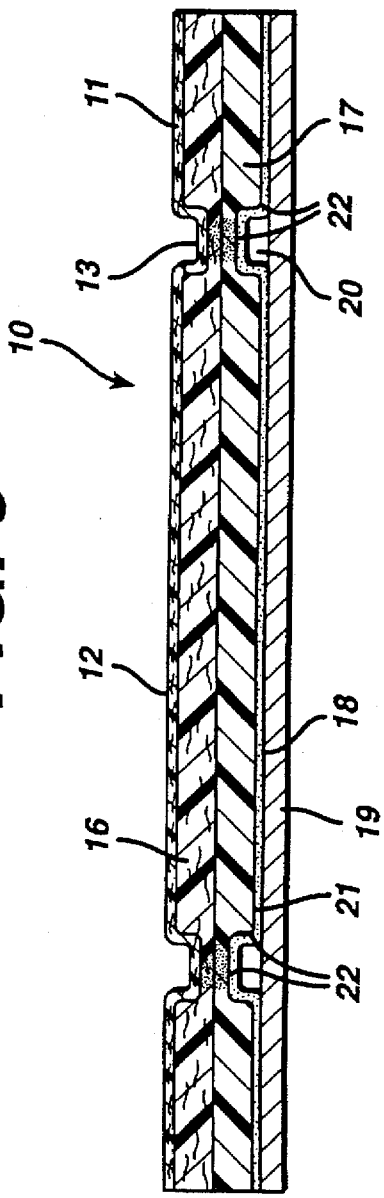
FIG. 5 is a cross-section taken along line 5—5 of FIG. 1.

Referring to FIG. 5, the pad 10 is constructed with a cover layer 11 having a body-contacting surface 12. In one embodiment, cover layer 11 comprises a nonwoven fibrous web formed of staple hydrophobic textile fibers. Such fibers may be unified by being coated with a water-insoluble rubbery fiber-binding resin so that all of the individual fibers are substantially covered with a resin coat, thus bonding them together at their crossing points while leaving the interstices of the web unfilled.

The cover layer 11 can also be made from a porous, substantially planar flexible polymeric coating on the surface of a bonded staple hydrophobic fiber web or the outermost surface of a lofty web of blended fibers in an integral pad construction. Such a surface, due to the flatness of the polymeric coating, has an unusually soft, smooth feeling and is pleasing to the touch.

It is, however, preferable that the fibers of cover layer 11 be thermoplastic or, more preferable, a mixture of two or more types of thermoplastic fibers having different melting points. Upon application of heat and pressure sufficient to melt at least one of the fiber types, the remaining unmelted fibers will be thermobonded or fused together into a porous web. This processing step is described more fully in U.S. Pat. No. 4,622,089, Lauritzen, hereby incorporated by reference.

The fibrous materials found to be satisfactory in the making of cover layer 11 have been found to be blends of two thermoplastic fibers having distinguishable melting temperatures. Bicomponent fibers, fibers with an inner core of a thermoplastic fiber, e.g., polyester, surrounded by an outer sheath of thermoplastic, e.g., polyethylene, having a melting point much lower than the core, have been found to be the best fibers to work with from processing and performance standpoints. Such fibrous materials are taught by U.S. Pat. No. 4,622,089, Lauritzen. It is also conceivable that the materials for cover layer 11 may be coformed blends of pulp fluff and thermoplastic fibers, e.g., polypropylene.

It has been found to be acceptable to use fibrous materials for cover layer 11 having a denier in the range of from about 1.0 to about 4.0. Superior performance, from the standpoint of comfort, is believed to result from a denier of from about 1.5 to about 3.5 or, most preferably, from a denier of about 1.5 to about 2.0. Currently, commercialization is about to begin with a denier of 1.8.

Fiber length for cover layer 11 has been found to be satisfactory if in the range of from about 0.5 inches to about 2.5 inches.

The resulting web is a thin, pliable, resilient, porous, cloth-like fabric whose top surface has a soft, smooth, pleasing, tactile quality. This web may be fed directly and continuously into the manufacturing process for the pad 10 of this invention. Or, it may be collected and stored for later use.

Immediately below and in heat bonded relationship with cover layer 11 is an absorbent layer 16 comprising a blend of thermoplastic fibers. It is preferable that the thermoplastic fibers of absorbent layer 16 be a mixture of two or more types of thermoplastic fibers having different melting points. Bicomponent fibers, fibers with an inner core of a thermoplastic fiber, e.g., polyester, surrounded by an outer sheath of thermoplastic, e.g., polyethylene, having a melting point much lower than the core, have been found to be the best fibers to work with from processing and performance standpoints. Like cover layer 11 above it, upon application of heat and pressure sufficient to melt at least one of the fiber types, the remaining unmelted fibers will be thermobonded or fused together into a porous web.

It is also preferable to include cellulosic pulp fibers with the thermoplastic fibers in absorbent layer 16. Since thermoplastic fibers, without further treatment, are essentially hydrophobic, absorbent layer 16 will not effectively draw fluid away from cover layer 11 absent some hydrophilic material. It is important to have sufficient pulp to absorb fluid. However, as will be described more fully below, it is also important to have a sufficient amount of thermoplastic fibers so that, when the layer is heat bonded (as will be described more fully below) there will be sufficient melting of thermoplastic to fill the interstitial void space in the web. An acceptable amount of pulp for effective absorbency is from about 20% to about 95% by weight. Conversely, an acceptable amount of thermoplastic fibers is from about 5% to about 80% by weight. A preferred amount of pulp would be in the range of from about 20% to about 60% by weight (with thermoplastic fibers being in the range of from about 40% to about 80%). A more preferred amount of pulp would be in the range of from about 20% to about 40% by weight (with thermoplastic fibers being in the range of from about 60% to about 80%).

Another way to characterize the ratio of thermoplastic to pulp is to look at the total amount of pulp and thermoplastic fibers in both cover layer 11 and absorbent layer 16. Since they are to be in heat bonded relationship, and (as will be described more fully below) it is desirable for some of the thermoplastic fibers in each layer to melt and fuse with each other, it is preferable that, when bonding cover layer 11 together with absorbent layer 16, there is at least 35% by weight thermoplastic fibers. It is more preferable that there be at least 60% by weight thermoplastic fibers in both layers.

Upon formation of the absorbent layer 16, the material may be fed directly and continuously into the manufacturing process for the pad 10 of this invention or it may be collected and used later. Bonding between the cover layer 11 and the absorbent layer 16 is accomplished by placing the layers in contact with each other and subjecting them to pressure and heat. This causes further melting of the fibers of the cover layer 11 and absorbent layer 16 resulting in thermobonding of the layers to each other upon cooling. This process is described more fully below.

It will, of course, be appreciated that the absorptive portion of the shield may be the central portion of an integrally formed pad member having a porous, planar, flexible polymeric coating as its top surface. In other embodiments of the present invention, the absorptive portion of the shield can utilize a variety of water immobilizing materials, e.g., superabsorbing polymers or peat moss, to increase fluid capacity or minimize pad bulk. Such materials are taught by Y. Levesque in U.S. Pat. No. 4,507,122; S. Dabi in U.S. Pat. No. 4,494,963; by I. S. Ness in U.S. Pat. No. 4,880,419; by J. Roller in U.S. Pat. No. 4,443,492; hereby incorporated by reference.

The fusible fibrous materials found to be satisfactory in the making of absorbent layer 16 are the same fibrous materials used for cover layer 11. Bicomponent polyester/polyethylene fibers have been found to be the best fibers to work with from processing and performance standpoints. Although it has been found that using fibers having a denier of about 1.8 in cover layer 11 results in improved comfort, it is not necessary to use fibers of this denier for absorbent layer 16. Although any denier in the range of from about 1.0 to about 4.0 will suffice, from a cost standpoint a denier of from about 2.5 to about 3.5 or more preferably, a denier of about 3.0 will yield good performance with acceptable manufacturing costs.

Fiber length for absorbent layer 16 has been found to be satisfactory if in the range of from about 0.5 inches to about 2.5 inches.

It is clear that the major distinctions between cover layer 11 and absorbent layer 16 is the presence of pulp in absorbent layer 16 and the possibility of finer denier fibers in cover layer 11. However, since the ranges for denier for each layer overlap, it is possible and acceptable to use the same denier fibers for both the cover layer 11 and absorbent layer 16. In such a case, there is no real need for two separate and distinct layers. Instead, it is possible to construct the pad using one layer that has a body contacting surface and a surface which faces barrier layer 17 (which is described in more detail below). In such a case, however, it is important to remember that the body contacting surface should be devoid of pulp. One of the main functions of the body contacting surface is to provide an essentially hydrophobic surface so that fluid will not remain at the surface but will instead be drawn to the absorbent material below. Therefore, when constructing a pad having one layer (instead of the two heretofore taught) the web should be laid with 100% thermoplastic fibers for at least the first mil. Thereafter, the mixtures of pulp and thermoplastic fibers taught above should be used.

Immediately beneath and in heat bonded relationship with absorbent layer 16 is a barrier layer 17 in the form of a soft, pliable, fluid impermeable layer. Such layers can be either vapor permeable or vapor impermeable and are well known in the art. Such barriers are commonly a mixture of two thermoplastic materials such as polyethylene and low melt EVA. U.S. Pat. No. 4,731,066 by R. Korpman adequately teaches such barrier layers and is hereby incorporated by reference.

Typically, the barrier layer 17 is purchased and fed from rolls into the manufacturing process for pad 10. The barrier layer 17 is brought into contact with the surface of absorbent layer 16 opposite the cover layer 11. Bonding between the barrier layer 17 and the absorbent layer 16 is accomplished by subjecting them to pressure and heat. This causes further melting of the fibers of the absorbent layer 16 resulting in thermobonding of the layers to each other upon cooling. This bonding step, described more fully below, may be done at the same time as the bonding step between cover layer 11 and absorbent layer 16.

Improved contact between absorbent layer 16 and barrier 17 would result if an adhesive coating were applied to either layer before they were put together. These adhesives are not necessary at the areas where pressure and heat is applied to bond the layers together. However, in those areas where bonding does not take place, adhesives will improve the contact between the layers. Such adhesives are well known in the art. An example would be U.S. Pat. No. 4,526,577, hereby incorporated by reference.

Applying adhesive to at least 20 percent of the surface area between absorbent layer 16 and barrier layer 17 will result in adequate bonding. Preferably adhesive should be applied to at least 50 percent of the surface area. However, it should be noted that every incremental increase in adhesive coverage will either improve the contact, or at least make delayering less likely.

Adhesive layer 18 comprises, typically, a pressure sensitive adhesive, is known in the art and is adequately taught in U.S. Pat. No. 4,554,191 by R. Korpman and in U.S. Pat. No. 4,335,026 by I. J. Bilinth, hereby incorporated by reference. Adhesive layer 18 keeps the pad properly positioned on the wearer's underpants during use. It is attached to barrier layer 17 and, for packaging is covered with a release paper 19 that is easily removed just prior to use.

In order for the adhesive of adhesive layer 18 to function effectively under the conditions to which it is subjected and on the fabrics it will be contacting, not only is the selection of the adhesive itself important but also the intricate adhesive system must be balanced as to surface adhesion, compliancy, coating weight, backing adhesion and backing strength. To remove cleanly from the garment to which it is attached, the adhesive bond to the garment surface must be weaker than the cohesive strength of the adhesive per se, the bond strength of the adhesive to its backing material, and the intrinsic strength of the composite structure.

The adhesive layer 18 preferably comprises an adhesive, either moisture vapor permeable or moisture vapor impermeable, which can be securely attached to fabrics normally made into undergarments and is capable of being easily removed therefrom without fabric damage or leaving noticeable adhesive residue thereon.

Adhesive layer 18 is commonly applied by a transfer coating process wherein the adhesive layer 18 is first applied to release paper 19, and the adhesive/release paper combination is then applied to backing layer 17. The release paper 19 is well known in the art and is usually coated with a silicone resin, as silicone coatings have relatively low release energies in comparison with, for instance, backing layer 17 materials.

Figure 6:
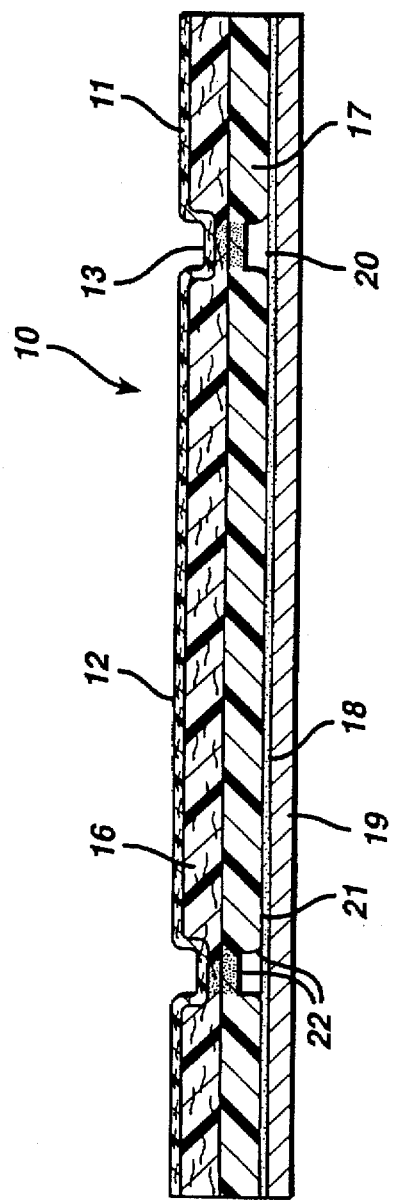
FIG. 6 is a cross-section of a pad of the prior art.

Because the release paper 19 has a lower release energy than backing layer 17, adhesive layer 18 will preferentially stick to backing layer 17 when the release paper 19 is removed. For this to be the case, it is important to keep in mind that, when applying adhesive layer 18 to backing layer 17, the adhesive that is deposited must make contact with backing layer 17. This is not usually a problem, because the backing layer 17 is generally planar. However, when fluid barriers 13 and 14 are formed, recesses 20 develop in the garment side surface 21 of backing layer 17. Using a normal transfer coating process, the adhesive layer 18 will not make contact with the recess surfaces 22, as can be seen in FIG. 6. Thus, adhesive layer 18 will bridge the recess 20.

As a consequence of bridging the recess 20, adhesive layer 18 will either adhere to, and be removed by, release paper 19 when it is removed. Or, if there is sufficient integrity in the adhesive, the adhesive will make contact with the wearer's clothes and will remain on them when the pad is removed. Thus, it is important for adhesive layer 18 to follow the contours of backing layer 17, including the recesses 20 to prevent this from happening.

Of additional importance, when fluid barriers 13 and 14 are formed, small holes may develop in backing layer 17. By applying adhesive layer 18 such that it makes contact with the recess surfaces 22, the adhesive will effectively plug these holes keeping the barrier integrity of backing layer 17 intact.

Figure 7:
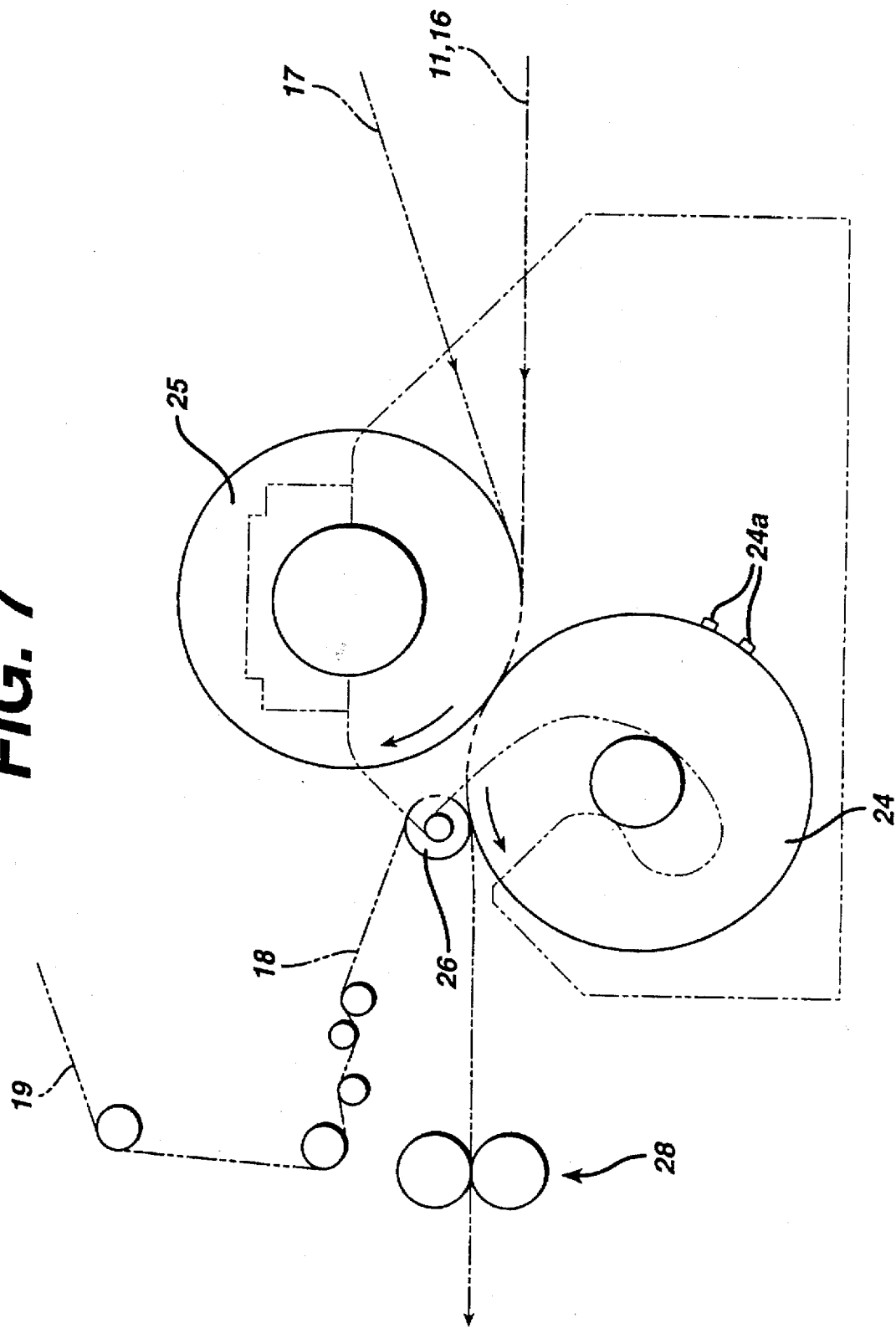
FIG. 7 is a schematic drawing of the manufacturing process of the present invention.

The component parts of the pad 10 are assembled and unified by heat-sealing according to the schematic diagram illustrated in FIG. 7. Pad 10 is then trimmed to shape and size along the outer fluid barrier 13.

The process begins by placing cover layer 11 and absorbent layer 16 together. The two layers may, optionally, be fed into a pattern embosser (not shown) which prints a pattern onto the cover layer 11. The backing layer 17 is then fed to the cover layer/absorbent layer combination. For secure contact, an adhesive may be applied (not shown) just prior to applying the backing layer 17. If adhesive is applied it is preferred that the three layers be subjected to slight pressure to assure adequate contact between the backing layer 17 and the absorbent layer 16.

The pad material is then fed into a sealing station 23 where pressure and heat are applied. The pressure and heat are controlled such that the temperature exceed the lower melting point of the thermoplastic materials in cover layer 11, absorbent layer 16, and barrier layer 17, but does not exceed the melting point of the remaining thermoplastic materials in each of the three layers.

The sealing station 23 is comprised of a pattern roll 24, an anvil roll 25, and a transfer roll 26. The pattern roll 24 is a cylindrical roll having raised surfaces 24a that imparts the pattern of the fluid barriers 13 and 24 on the pad material as it passes between the pattern roll 24 and the anvil roll 25. After exiting the nip between the pattern roll 24 and the anvil roll 25, the pad material remains in contact with the pattern roll 24 which has the benefit of increasing the dwell time that the fluid barriers 13 and 14 are exposed to heat.

It is important to note that, while higher temperatures and pressures are beneficial from the standpoint of fusing the layers together, if the temperature and/or pressure is too high then too many pin holes will develop in the pad structure which will lead to failure. For instance, in the case of producing 400–600 pads per minute, each pad comprised of polyester/polyethylene bicomponent fibers, it is important to keep the temperature of the pattern roll 24 within the range of from about 90° F. to about 400° F., preferably from about 100° F. to about 250° F.; and it is important to keep the temperature of the anvil roll 25 within the range of from about ambient to about 200° F., preferably from about 90° F. to about 150° F. Further, in an apparatus with two 6" diameter pressure cylinders, it is important to keep the pressure within the range of from about 1 to about 600 psi, preferably within the range of from about 10 to about 150 psi. More preferably the pressure should be kept within the range of from about 10 to about 80 psi.

Another related variable is the gap distance between the pattern roll 24 and the anvil roll 25. As the gap distance decreases, fusing between the layers of the pad improves. However, at the same time the possibility of developing pin holes also increases. Therefore, in the case of polyester/ polyethylene bicomponent fibers, it is important to keep the gap distance less than about 0.2 inches. For relatively thin pads to be used as panty shields that gap distance is preferably between 0 and 0.005 inches. It should be kept in mind however, that the gap distance variable will be dependent upon the thickness of the resulted pad 10 and upon the thickness of the various layers making up pad 10.

The combination of adhesive layer 18 and release paper 19 is then applied by transfer roll 26. Transfer roll 26 is rollingly engaged with pattern roll 24 for a number of reasons. It is important to keep the pad material from slipping or losing registration with the raised surfaces or protuberances of pattern roll 24. Further, the transfer roll can impart a slight pressure on the pad material which forces the recesses 20 that were just formed to come into contact with adhesive layer 18 at the area of fluid barriers 13 and 14. Thus, and even though the release paper 19 is generally not elastic and will not follow the contours of recess 20, the adhesive layer 18 will. The transfer roll 26 is preferably elastomeric, more preferably silicone, with a durometer from about 20 to about 70, more preferably from about 35 to about 55. The pressure exerted by the transfer roll 26 are generally in the range of from about 0 to about 200 psi, more preferably in the range of from about 50 to about 150 psi. Higher pressures may be used, but this will cause the transfer roll 26 to fatigue and prematurely wear.

After applying the adhesive layer 18 and release paper 19, it may be necessary to further calender 28 the pad material. Since the only real contact at transfer roll 26 was in relation to the raised pattern of pattern roll 24, adhesive layer 18 may be in firm contact with backing layer 17 only at fluid barriers 13 and 14. Thus, a further calendar step will ensure adequate contact between adhesive layer 18 and backing layer 17 at other points. It is important to point out that it is not preferable to try to use calender 28 to force contact between adhesive layer 18 and backing layer 17 at the location of fluid barriers 13 and 14, because the pressures necessary to force contact would crush the remainder of the pad and reduce its absorbent performance.

After exiting the calender 28, the pad material is then fed into a cutting station (not shown). Thereafter, excess trim material is removed and the final pad 10 is packaged.

It should be noted that pad 10 may be trimmed as close to outer fluid barrier 13 as possible without actually removing any of the fused material in the barrier. However, it is preferential to leave some portion of unfused material along the outer perimeter. This unfused material is less dense than the fused fluid barrier 13 and is considerably softer to the touch.

What is claimed is:

1. A process for applying a layer of adhesive onto a substrate having at least one surface containing at least one recess, wherein each of said at least one recess comprises a bottom surface that is not in the same plane as the at least one surface of the substrate, the process comprising the steps of:

a. applying a layer of adhesive to a transfer layer;
   b. bringing the adhesive layer into contact with the at least one recess containing surface of the substrate; and
   c. applying sufficient pressure across the transfer layer and the bottom surface of the at least one recess to force the adhesive layer into contact with the bottom surface of the at least one recess, wherein the pressure is applied in a pattern corresponding to the at least one recess in the at least one surface of the substrate, whereby the adhesive layer follows the contours of the at least one recess-containing surface.

2. The process of claim 1 further comprising the step of calendering the substrate.

3. The process of claim 1 wherein the pressure is applied in a pattern by means of a pattern roll, and the pattern roll is operated at a temperature of from about 90° F. to about 400° F.

4. The process of claim 3 wherein the pressure applied is within the range from 1 to 600 psi when using an apparatus with two 6 inch diameter pressure cylinders.

5. The process of claim 1 wherein the at least one recess is arranged in a pattern and the pressure is applied in a pattern with at least one raised surface arranged in a pattern that matches and coincides with the pattern of the at least one recess.

6. The process of claim 1 wherein the substrate has a second surface in opposite relationship to the at least one surface and wherein pressure is also applied to the second surface.

7. The process of claim 1 further comprising the step of applying pressure to the at least one surface of the substrate that is insufficient to force the adhesive layer into contact with the bottom surface of the at least one recess.

* * * * *